(12) United States Patent
Scharf et al.

(10) Patent No.: US 6,706,209 B1
(45) Date of Patent: Mar. 16, 2004

(54) STABILIZED MONOMER COMPOSITION

(75) Inventors: Jakob Scharf, Worms (DE); Hartmut Rau, Osthofen (DE); Friedrich Goetzen, Worms (DE)

(73) Assignee: Roehm GmbH & Co. KG, Darmstadt (DE)

( * ) Notice: Subject to any disclaimer, the term of this patent is extended or adjusted under 35 U.S.C. 154(b) by 293 days.

(21) Appl. No.: 09/644,556

(22) Filed: Aug. 24, 2000

(30) Foreign Application Priority Data

Aug. 27, 1999 (DE) .......................................... 199 40 623

(51) Int. Cl.[7] .......................... C09K 3/00; C09K 15/08
(52) U.S. Cl. .......................... 252/183.11; 252/183.12; 252/403; 252/404
(58) Field of Search .................. 252/183.11, 183.12, 252/403, 404, 182.29

(56) References Cited

U.S. PATENT DOCUMENTS 4,956,020 A    9/1990  Nakajima
6,020,385 A  * 2/2000  Halle ........................... 521/31

FOREIGN PATENT DOCUMENTS

| EP | 0 266 906 | 5/1988 |
| EP | 0 467 850 | 1/1992 |
| EP | 0 924 228 | 6/1999 |
| WO | WO 89/10343 | 11/1989 |

* cited by examiner

Primary Examiner—Cephia D. Toomer
(74) Attorney, Agent, or Firm—Oblon, Spivak, McClelland, Maier & Neustadt, P.C.

(57) ABSTRACT

A stabilized monomer composition containing at least one ethylenically unsaturated monomer and a combination of N,N-diethylhydroxylamine an N-nitroso-N-phenylhydroxylamine or its salt in a weight ratio of from 1:1 to 10:1 permits the synthesis of 2-hydroxyalkyl (meth) acrylates in particularly high yields and remains stable during prolonged storage.

36 Claims, No Drawings

STABILIZED MONOMER COMPOSITION

BACKGROUND OF THE INVENTION

1. Field of the Invention

The present invention relates to a stabilized monomer composition that includes N,N-diethylhydroxylamine and N-nitroso-N-phenylhydroxyl amine or its salt and to processes for synthesis and purification of a stabilized monomer composition.

2. Discussion of the Background

Stabilization of monomer compositions is a widely recognized problem. For example, methacrylic acid derivatives exhibit undesired premature polymerization. The polymerization rate increases strongly, especially at elevated temperatures. However, many processes for synthesis of acrylic monomers typically include process steps such as distillation, in which the temperature is elevated. To ensure that these purification processes can nevertheless be achieved, the monomers to be purified must be stabilized. In addition, prolonged storage leads to polymerization of the monomers. Such aging phenomena occur especially under exposure to light.

It is indeed possible to reduce such polymerization by addition of high concentrations of known inhibitors. However, the consequence is that the desired polymerization can then only be achieved by addition of correspondingly high concentrations of initiators. If the inhibitor is added in an extremely high concentration, it must be separated prior to polymerization. Otherwise it is impossible to achieve high molecular weights. For this reason, the lowest possible inhibitor concentrations should be used.

Known polymerization inhibitors for acrylates include, for example, phenothiazine, hydroquinone, especially hydroquinone monomethyl ether and benzoquinone. The use of N,N-diethylhydroxylamine is also known. European Patent Application EP A 0266906 discloses the synergistic activity of hydroxylamines in combination with phenylenediamines. It has been found, however, that this combination alone is inadequate in processes for synthesis of hydroxyalkyl (meth) acrylates. Thus yield losses are suffered in particular during purification by distillation.

SUMMARY OF THE INVENTION

Accordingly, one object of the present invention is to provide a stabilized monomer composition which remains stable during prolonged storage. It is also an object to achieve high degrees of polymerization without separation of the inhibitor by, for example, addition of initiators.

A further object of the invention is to find a stabilized monomer composition which is suitable in particular for distillation.

Yet another object of the invention is to find compositions which permit a high product yield during the synthesis of hydroxyalkyl (meth)acrylates.

These and other objects of the invention have been satisfied by the discovery of a stabilized monomer composition, comprising:

at least one ethylenically unsaturated monomer;
N,N-diethylhydroxylamine; and
N-nitroso-N-phenylhydroxylamine or its salt;
wherein a weight ratio of N,N-diethylhydroxylamine to N-nitroso-N-phenylhydroxylamine or its salt is from 1:1 to 10:1, and by the discovery of methods for its preparation and its use in purifying 2-hydroxyalkyl (meth)acrylates.

DETAILED DESCRIPTION OF THE INVENTION

The first embodiment of the present invention includes a stabilized monomer composition, comprising:

at least one ethylenically unsaturated monomer;
N,N-diethylhydroxylamine; and
N-nitroso-N-phenylhydroxylamine or its salt;
wherein a weight ratio of N,N-diethylhydroxylamine to N-nitroso-N-phenylhydroxylamine or its salt is from 1:1 to 10:1.

Another embodiment of the invention includes a process for synthesis of a stabilized monomer composition, comprising:

mixing at least one ethylenically unsaturated monomer, N,N-diethylhydroxylamine and N-nitroso-N-phenylhydroxylamine or its salt;
wherein a weight ratio of N,N-diethylhydroxylamine to N-nitroso-N-phenylhydroxylamine or its salt is from 1:1 to 10:1.

A third embodiment of the invention includes a process for synthesis of a 2-hydroxyalkyl (meth)acrylate, comprising:

reacting an oxirane compound with (meth)acrylic acid in the presence of a catalyst;
adding at least one inhibitor;
adding an aqueous solution of N,N-diethylhydroxylamine and N-nitroso-N-phenylhydroxylamine or its salt, thereby providing a mixture; and
distilling said mixture.

A fourth embodiment of the invention includes a method of purifying a 2-hydroxyalkyl (meth)acrylate, comprising:

adding at least one inhibitor to said 2-hydroxyalkyl (meth)acrylate:
adding an aqueous solution of N,N-diethylhydroxylamine and N-nitroso-N-phenylhydroxylamine or its salt, thereby providing a mixture; and
distilling said mixture.

In particular the following advantages are achieved by the inventive steps:

Monomer compositions stabilized according to the invention remain stable during prolonged storage even if exposed to light.

Monomers stabilized according to the present invention can be purified particularly easily by distillation.

Stabilized monomer compositions can also be transformed by known reactions, in which the monomer is modified while preserving the ethylenically unsaturated double bond and ensuring that this transformation does not lead to particularly high losses of yield.

It is very surprising that even monomers existing in the gas phase can be stabilized by the inventive combination.

Ethylenically unsaturated monomers are compounds which contain at least one, double bond that can undergo radical polymerization. These ethylenically unsaturated monomers include among others vinyl esters; (meth)acrylic acid; (meth)acrylic acid esters such as methyl and ethyl (meth)acrylate; vinyl chloride; vinylidene chloride; vinyl acetate; styrene; substituted styrenes with an alkyl substituent in the side chain, such as α-methylstyrene and α-ethylstyrene; substituted styrenes with an alkyl substituent on the ring, such as vinyltoluene and p-methylstyrene;

halogenated styrenes, such as monochlorostyrenes, dichlorostyrenes, tribromostyrenes and tetrabromostyrenes; vinyl and isopropenyl ethers; maleic acid derivatives, such as maleic anhydride, methylmaleic anhydride, maleimide, methylmaleimide; and dienes, such as divinylbenzene.

The notation (meth)acrylic derivatives includes methacrylic derivatives, acrylic derivatives and mixtures of the two.

Preferred ethylenically unsaturated monomers are (meth)acrylic acid as well as derivatives of (meth)acrylic acid. These compounds can be represented by, for example, Formula I

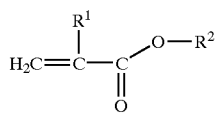

where $R^1$ denotes hydrogen or a methyl group, $R^2$ denotes hydrogen, an aryl group, which can also contain hetero atoms, such as phenyl and imidazole, or a straight-chain, branched or cyclic alkyl group with up to 30 carbon atoms, which may or may not be saturated, and which can also contain hetero atoms such as nitrogen and/or oxygen, examples being methyl, ethyl, propyl, butyl, pentyl, hexyl, cyclopentyl, cyclohexyl, isobornyl, vinyl, propenyl, butynyl, 2-(N,N-dimethylamino)ethyl, 2-(N,N-dimethylamino)propyl, 2-hydroxypropyl and 2-hydroxyethyl.

Preferably, the ethylenically unsaturated monomers include methyl (meth)acrylate, ethyl (meth)acrylate, propyl (meth)acrylate, isopropyl (meth)acrylate, n-butyl (meth)acrylate, isobornyl (meth)acrylate, hydroxyalkyl (meth)acrylates, such as 2-hydroxyethyl (meth)acrylate, 2-hydroxypropyl (meth)acrylate, 3-hydroxypropyl (meth)acrylate and 3,4-dihydroxybutyl (meth)acrylate, as well as aminoalkyl (meth)acrylates, such as dimethylaminoethyl methacrylate (DMAEMA).

The (meth)acrylic acid amides corresponding to the (meth)acrylic acid esters also comprise a preferred group of ethylenically unsaturated monomers. An example of this group is N-dimethylaminopropyl methacrylamide (DMAPMA).

The ethylenically unsaturated monomers can be present individually or as mixtures in the inventive composition.

The compounds N,N-diethylhydroxylamine and N-nitroso-N-phenylhydroxylamine ("cupferron") are widely known among those skilled in the art and are commercially available from numerous suppliers. N-nitroso-N-phenylhydroxylamine is an acid compound whose salts, such as the ammonium, aluminum, copper, lithium, sodium, potassium and rubidium salts, are also intended to be included in the present invention.

Preferably the weight ratio of N,N-diethylhydroxylamine to N-nitroso-N-phenylhydroxylamine or its salt ranges from 1:1 to 10:1. The weight ratio includes all values and subvalues therebetween, especially including 2:1, 3:1, 4:1, 5:1, 6:1, 7:1, 8:1, and 9:1. The concentration of N,N-diethylhydroxylamine preferably ranges from 10 to 500 ppm based on the total weight of the composition. The concentration of N,N-diethylhydroxylamine includes all values and subvalues therebetween, especially including 50, 100, 150, 200, 250, 300, 350, 400 and 450 ppm. N-nitroso-N-phenylhydroxylamine or its salt is preferably present in a concentration ranging from 10 to 500 ppm, in relative to the total weight of the composition. The concentration of N-nitroso-N-phenylhydroxylamine or its salt includes all values and subvalues therebetween, especially including 50, 100, 150, 200, 250, 300, 350, 400 and 450 ppm.

The lower limit value is determined by the shelf life of the stabilized monomer composition. If the respective compound with stabilizing effect is used in a concentration of less than 10 ppm, the shelf life will be inadequate for many purposes. If only relatively little stabilization of the monomer composition is desired, even lower concentrations can be used.

The upper limit value is determined on the one hand by economic viewpoints, while on the other hand it should be possible to achieve the desired polymerization, started by initiators. Accordingly, the upper limit value has been found to be an advantageous embodiment, which should not be construed as limiting.

The inventive composition can contain further inhibitors. These are widely known among those skilled in the art. For example, 1,4-dihydroxybenzenes can also be added for stabilization. Dihydroxybenzenes with different substituent positions can also be used. In general, such inhibitors can be represented by general Formula (II)

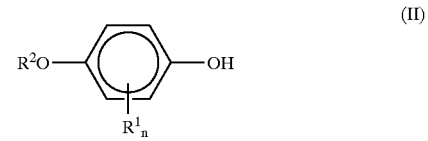

$R^1$ denotes a straight-chain or branched alkyl group with one to eight carbon atoms, halogen or aryl, preferably an alkyl group with one to four carbon atoms, especially preferably methyl, ethyl, n-propyl, isopropyl, n-butyl, isobutyl, sec-butyl, tert-butyl, Cl, F or Br;

n is an integer ranging from one to four, preferably one or two; and $R^2$ denotes hydrogen, a straight-chain or branched alkyl group with one to eight carbon atoms or aryl, preferably an alkyl group with one to four carbon atoms, especially preferably methyl, ethyl, n-propyl, isopropyl, n-butyl, isobutyl, sec-butyl or tert-butyl.

Compounds with 1,4-benzoquinone can also be used as the parent compound. These can be described by Formula (III)

where

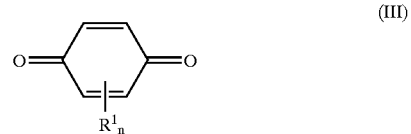

$R^1$ denotes a straight-chain or branched alkyl group with one to eight carbon atoms, halogen or aryl, preferably an alkyl group with one to four carbon atoms, especially preferably methyl, ethyl, n-propyl, isopropyl, n-butyl, isobutyl, sec-butyl, tert-butyl, Cl, F or Br; and n is an integer ranging from one to four, preferably one or two.

Furthermore, phenols of general structure (IV) can be used:

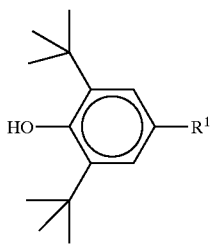

(IV)

where
R¹ denotes a straight-chain or branched alkyl group with one to eight carbon atoms, aryl or aralkyl, propionic acid esters with monohydric to tetrahydric alcohols, which can also contain hetero atoms such as S, O and N, preferably an alkyl group with one to four carbon atoms, especially preferably methyl, ethyl, n-propyl, isopropyl, n-butyl, isobutyl, sec-butyl, tertbutyl.

A further advantageous substance class comprises sterically hindered phenols based on triazine derivatives of Formula (V)

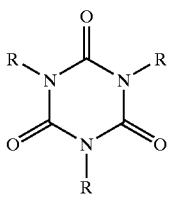

(V)

where
R=compound of Formula (VI)

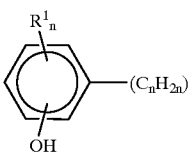

(VI)

where
$R^1=C_nH_{2n+1}$,
with n=1 or 2.

A further group of known inhibitors and antioxidants comprises amines, especially sterically hindered amines.

This group includes in particular phenylenediamines, which can be represented by Formula (VII)

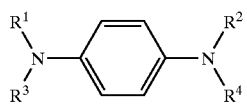

(VII).

where $R^1$, $R^2$, $R^3$ and $R^4$ independently denote hydrogen or alkyl, aryl, alkaryl, aralkyl groups, each with up to 40, preferably up to 20 carbon atoms, preferably at least one of the groups $R^1$, $R^2$, $R^3$ and $R^4$ being hydrogen.

Examples of p-phenylenediamines include p-phenylenediamine in which the groups $R^1$, $R^2$, $R^3$ and $R^4$ are hydrogen; N-phenyl-N'-alkyl-p-phenylenediamines such as N-phenyl-N'-methyl-p-phenylenediamine, N-phenyl-N'-ethyl-p-phenylenediamine, N-phenyl-N'-propyl-p-phenylenediamine, N-phenyl-N'-isopropyl-p-phenylenediamine, N-phenyl-N'-n-butyl-p-phenylenediamine, N-phenyl-N'-isobutyl-p-phenylenediamine, N-phenyl-N'-sec-butyl-phenylenediamine, N-phenyl-N'-tert-butyl-p-phenylenediamine, N-phenyl-N'-n-pentyl-p-phenylenediamine, N-phenyl-N'-n-hexyl-p-phenylenediamine, N-phenyl-N'-(1-methylhexyl)-p-phenylenediamine, N-phenyl-N'-(1,3-dimethylbutyl)-p-phenylenediamine and N-phenyl-N'-(1,4-dimethylpentyl)-p-phenylenediamine;

N-phenyl-N',N'-dialkyl-p-phenylenediamines, such as N-phenyl-N',N'dimethyl-p-phenylenediamine, N-phenyl-N', N'-diethyl-p-phenylenediamine, N-phenyl-N', N'-di-n-butyl-p-phenylenediamine, N-phenyl-N',N'-di-sec-butyl-phenylenediamine and N-phenyl-N'-methyl-N'-ethyl-p-phenylenediamine;

N,N-dialkyl-p-phenylenediamines, such as N,N-dimethyl-p-phenylenediamine and N,N'-diethyl-p-phenylenediamine;

N,N'-dialkyl-p-phenylenediamines, such as N,N'-diisopropyl-p-phenylenediamine and N,N'-diisobutyl-p-phenylenediamine;

N,N'-diaryl-phenylenediamines, such as N,N'-diphenyl-p-phenylenediamine;

N,N,N'-trialkyl-p-phenylenediamines, such as N,N,N'-trimethyl-p-phenylenediamine and N,N,N'-triethyl-p-phenylenediamine.

A further preferred group of inhibitors and antioxidants are phenazine dyes. They include in particular induline and nigrosine. Nigrosine is obtained by heating nitrobenzene, aniline and aniline hydrochloride with metallic iron and $FeCl_3$. For this purpose alcohol-soluble aniline dyes, which can have, for example, 5 benzene rings, such as dianilido-N,N-diphenylphenosafranine are preferred. These substances are widely known and can be obtained commercially.

There are used especially successfully the compounds 1,4-dihydroxybenzene, 4-methoxyphenol, 2,5-dichloro-3,6-dihydroxy-1,4-benzoquinone, 1,3,5-trimethyl-2,4,6-tris(3,5-di-tert-butyl4-hydroxybenzyl )benzene, 2,6-ditert-butyl-4-methylphenol, 2,4-dimethyl-6-tertbutylphenol, 2,2-bis[3,5-bis(1,1-dimethylethyl)-4-hydroxyphenyl-1-oxoperepoxymethyl)]-1, 3-propanediyl ester,2,2'-thiodiethylbis[3-(3,5-di-tert-butyl-4-hydroxyphenyl)] propionate, octadecyl-3-(3,5-di-tertbutyl-4-hydroxyphenyl) propionate, 3,5-bis(1,1-dimethylethyl-2,2-methylenebis(4-methyl-6-tertbutyl)phenol, tris-(4-tert-butyl-3-hydroxy-2,6-dimethylbenzyl)-s-triazine-2,4,6-(1H,3H,5H)trione, tris(3, 5-di-tert-butyl4-hydroxy)-s-triazine-2,4,6-(1H,3H,5H) trione, tert-butyl-3,5-dihydroxybenzene or diphenyl-p-phenylenediamine (DPPD) in addition to N,N-diethylhydroxylamine and N-nitroso-N-phenylhydroxylamine.

Depending on purpose, there may be no need to use further inhibitors. The concentration of the additional inhibitors individually or as a mixture amounts to 0.01 to 0.5% by weight relative to the weight of the total composition, for many applications of the inventive composition.

Many of these inhibitors are commercially available.

The inventive stabilized monomer compositions can contain further constituents.

These include solvents, preferably benzene, toluene, n-hexane, cyclohexane, methyl isobutyl ketone and methyl ethyl ketone.

Also preferred components of the inventive composition are known adjuvants such as anti-binding agents, antistatics, antioxidants, biostabilizers, chemical propellants, mold-release agents, flame retardants, lubricants, dyes, casting improvement agents, fillers, slip additives, adhesion promoters, catalysts, photostabilizers, optical brighteners, organic phosphorus compounds, oils, pigments, impact toughness improvers, reinforcing agents, reinforcing fibers, anti-weathering agents and plasticizers.

The inventive compositions can be obtained by mixing at least one ethylenically unsaturated monomer and a combination of N,N-diethylhydroxylamine and N-nitroso-N-phenylhydroxylamine or its salt in concentrations as defined above.

Further generally known inhibitors and antioxidants, such as hydroquinone monomethyl ether and DPPD, can also be added for this purpose.

The inventive compounds can be used, for example, to stabilize reaction mixtures during purification. It has been found that, by addition of a combination of N,N-diethylhydroxylamine and N-nitroso-N-phenylhydroxylamine or its salt, an extremely effective stabilization during thermal loading of the type that can occur during purification by distillation is achieved.

Furthermore, the inventive compositions are particularly suitable for producing 2-hydroxyalkyl (meth)acrylates. By the inhibition of undesired polymerization by means of the inventive combination of N,N-diethylhydroxylamine and N-nitroso-N-phenylhydroxylamine or its salt, both the (meth)acrylic acid reagents and the hydroxyalkyl (meth)acrylates obtained therefrom by reaction, for example with oxiranes, are prevented from undergoing radical polymerization.

These processes for synthesis of hydroxyalkyl (meth)acrylates, in which an oxirane compound is reacted with (meth)acrylic acid in the presence of an effective quantity of a catalyst and at least one compound having inhibiting effect, are described in, for example, European Patent EP A 0134133, British Patent GB 1195485, German Patent DE-PS 1911447 and Japanese Patent JP A 93-293285.

The oxirane compounds, which are also known as epoxides, include among others ethylene oxide, propylene oxide, 1,2-butylene oxide and/or 2,3-butylene oxide, cyclohexene oxide, styrene oxide, 1,2,3,4-diepoxybutane, 1,2,5,6-diepoxyhexane, epichlorohydrin and glycidyl esters. These compounds can be used either individually or as mixtures.

Examples of preferred catalysts of this reaction are chromium(III) compounds, such as chromium(III) carboxylates and chromium(III) alkoxides. They include among others chromium(III) hexanoate, chromium(III) pentanoate, chromium(III) butyrate, chromium(III) 2-ethylhexanoate, chromium(III) 2 -ethyidecanoate, chromium(III) oleate, chromium(III) stearate, chromium(III) acrylates, chromium (III) methacrylates, chromium(III) benzoates and chromium (III) acetate. Iron(III) compounds, such as iron(III) methacrylate, are also used for catalysis of the said reaction. Catalysts containing iron(III) and chromium(III) compounds are often used in combination.

The catalysts and oxirane compounds cited in the foregoing can generally be obtained commercially.

The reaction of (meth)acrylic acid with oxiranes takes place preferably at a temperature ranging from 15 to 90° C. and a pressure of from 1 to 5 bar. The temperature includes all values and subvalues therebetween, especially including 20, 30, 40, 50, 60, 70 and 80° C. The pressure includes all values and subvalues therebetween, especially including 1.5, 2, 2.5, 3, 3.5, 4 and 4.5 bar.

Furthermore, compositions containing in particular N-dimethylaminopropyl methacrylamide (DMAPMA) and/ or dimethylaminoethyl methacrylate (DMAEMA) are extremely stable during prolonged storage, although the added inhibitor can be overridden by initiators. For many applications, therefore, there is no need to separate the initiators prior to polymerization.

Having generally described this invention, a further understanding can be obtained by reference to certain specific examples which are provided herein for purposes of illustration only, and are not intended to be limiting unless otherwise specified.

EXAMPLES

Example 1

Distillation of 2-hydroxyethyl Acrylate Raw Ester

In a DS25 laboratory-scale thin-film evaporator (Normschliff Geraete GmbH, Wertheim) with 30 cm long silvered, packed column (6×6 mm V4A steel coils), automatic column head, product cooler, intensive cooler, vacuum unit and hose pump there was continuously distilled 6 kg of 2-hydroxyethyl acrylate raw ester. The raw ester was stabilized with 200 ppm of hydroquinone, 600 ppm of hydroquinone monomethyl ether, 200 ppm of diphenyl-p-phenylenediamine (DPPD) and 50 ppm of nigrosine (Nigrosine Base BA, Bayer AG).

According to GO analysis, the proportion of 2-hydroxyethyl acrylate was 84 wt %. The distillation was started after addition of 2.8 ml of an 85% aqueous solution (400 ppm) of N,N-diethylhydroxylamine and 50 ppm of cupferron (N-nitroso-N-phenylhydroxyl amine ammonium salt) in the form of 10% aqueous cupferron solution (3 ml).

No polymerization was observed within 8.5 hours at a product temperature of 130° C., a pressure in the range of 10 to 12 mbar and a rotor speed of 700 rpm.

The yield was 4800 g of 2-hydroxyethyl acrylate with a purity of 98.6% as determined by gas chromatography (GC). The purified product had an APHA color value of 6, as can be determined per DIN ISO 6271.

Comparison Example 1

Comparison Example 1 was carried out by the same procedure as for Example 1, except that only 50 ppm of cupferron was used, without addition of N,N-diethylhydroxylamine.

After 5 hours polymer formation look place in the distillation column, and so the distillation had to be stopped.

Furthermore, a reduced yield of 2430 g was recorded. The color value was 11, and the product purity was around 98.5% (GC).

Comparison Example 2

Comparison Example 2 was carried out by the same procedure as for Example 1, except that a mixture of 500 ppm of N,N-diethylhydroxylamine and 500 ppm of vitamin K (2-methyl-1,4naphthoquinone) was used for stabilization, without addition of cupferron.

In this case the formation of polymer in the column was so rapid that the experiment had to be stopped before relatively large quantities of 2-hydroxyethyl acrylate could be isolated.

The priority document of the present application, German patent application 19940623.5 filed Aug. 27, 1999, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A stabilized monomer composition, comprising:

A(i) at least one (meth)acrylic acid amide selected from the group consisting of N,N-dimethylaminopropyl methacrylamide, N,N-dimethylaminoethyl methacrylamide and a mixture thereof or (ii) at least one (meth) acrylic acid ester;

(B) N,N-diethylhydroxylamine; and (C) N-nitroso-N-phenylhydroxylamine or its salt;
wherein a weight ratio of N,N-diethylhydroxylamine to N-nitroso-N-phenylhydroxylamine or its salt is from 1:1 to 10:1;
wherein a concentration of N,N-diethylhydroxylamine is 10 to 500 ppm based on the total weight of said stabilized monomer composition; and
wherein a concentration of N-nitroso-N-phenylhydroxylamine or its salt is 10–500 ppm based on the total weight of said stabilized monomer composition.

2. The composition according to claim 1, wherein said salt of N-nitroso-N-phenylhydroxylamine is an ammonium salt, an aluminum salt, a copper salt, a lithium salt, a sodium salt, a potassium salt, or a rubidium salt.

3. The composition according to claim 1, further comprising an inhibitor and/or an antioxidant.

4. The composition according to claim 3, wherein said inhibitor is a dihydroxybenzene of Formula (II):

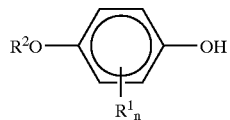

(II)

wherein $R^1$ is a straight-chain or branched alkyl group with one to eight carbon atoms, halogen or aryl;

n is an integer ranging from one to four; and $R^2$ is hydrogen, a straight-chain or branched alkyl group with one to eight carbon atoms or aryl.

5. The composition according to claim 3, wherein said inhibitor is a 1,4 benzoquinone of Formula (III):

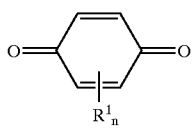

(III)

where $R^1$ is a straight-chain or branched alkyl group with one to eight carbon atoms, halogen or aryl; and n is an integer ranging from one to four.

6. The composition according to claim 3, wherein said inhibitor is a phenol of Formula (IV):

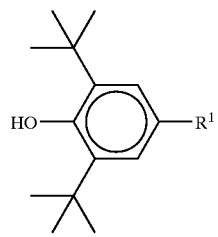

(IV)

wherein $R^1$ is a straight-chain or branched alkyl group with one to eight carbon atoms, aryl, aralkyl a propionic acid ester group with a monohydric to tetrahydric alcohol optionally containing hetero atoms.

7. The composition according to claim 3, wherein said inhibitor is a triazine derivative of Formula (V):

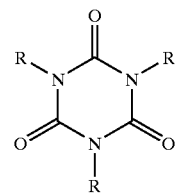

(V)

wherein

R=compound of Formula (VI)

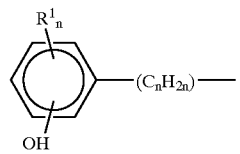

(VI)

wherein $R^1 = C_nH_{2n+1}$; and n=1 or 2.

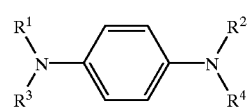

(VII).

8. The composition according to claim 3, wherein said inhibitor is a pheneylenediamine of Formula (VII):
wherein
$R^1$, $R^2$, $R^3$ and $R^4$ independently are hydrogen or alkyl, aryl, alkaryl, aralkyl groups, each with up to 40 carbon atoms.

9. The composition according to claim 8, wherein said phenylenediamine is selected from the group consisting of p-phenylenediamine, N-Phenyl-N'-alkyl-p-phenylene diamine, N-phenyl-N',N'-dialkyl-p-phenylenediamine, N,N-dialkyl-p-phenylenediamine, N,N'-dialkyl-p-phenylenediamine, N,N'-diaryl-phenylenediamine and N,N, N'-trialkyl-p-phenylenediamine.

10. The composition according to claim 3, wherein said inhibitor is a phenazine dye selected from the group consisting of induline and nigrosine.

11. The composition according to claim 3, wherein said inhibitor has a concentration of 0.01 to 0.5% by weight based on the total weight of said composition.

12. The composition according to claim 1, further comprising a solvent.

13. The composition according to claim 12, wherein said solvent is selected from the group consisting of benzene, toluene, n-hexane, cyclohexane, methyl isobutyl ketone, methyl ethyl ketone and mixtures thereof.

14. The composition according to claim 1, further comprising an adjuvant.

15. The composition according to claim 14, wherein said adjuvant is selected from the group consisting of an anti-binding agent, an antistatic, an antioxidant, a biostabilizer, a chemical propellant, a mold-release agent, a flame retardant, a lubricant, a dye, a casting improvement agent, a filler, a slip additive, an adhesion promoter, a catalyst, a photostabilizer, an optical brightener, an organic phosphorus compound, an oil, a pigment, an impact toughness improver, a reinforcing agent, a reinforcing fiber, an anti-weathering agent, a plasticizer and mixtures thereof.

16. A process for synthesis of a stabilized monomer composition, comprising:
mixing
(A) (i) at least one (meth)acrylic acid amide selected from the group consisting of N,N-dimethylaminopropyl methacrylamide, N,N-dimethylaminoethyl methacrylamide and a mixture thereof or (ii) at least one (meth)acrylic acid ester,
(B) N,N-diethylhydroxylamine, and
(C) N-nitroso-N-phenylhydroxylamine or its salt; and
adding an inhibitor and/or antioxidant;
wherein a weight ratio of N,N-diethylhydroxylamine to N-nitroso-N-phenylhydroxylamine or its salt is from 1:1 to 10:1;
wherein a concentration of N,N-diethylhydroxylamine is 10 to 500 ppm based on the total weight of said stabilized monomer composition; and
wherein a concentration of N-nitroso-N-phenylhydroxylamine or its salt is 10–500 ppm based on the total weight of said stabilized monomer composition.

17. The process according to claim 16, further comprising adding a solvent.

18. The process of claim 16, further comprising adding an adjuvant.

19. The process according to claim 16, wherein said (meth)acrylic acid ester is represented by Formula (I):

$$H_2C=\underset{R^1}{C}-\underset{\underset{O}{\|}}{C}-O-R^2$$

wherein
$R^1$ is hydrogen or a methyl group;
$R^2$ is an aryl group, an aryl group containing hetero atoms, a saturated or unsaturated straight-chain, branched or cyclic alkyl group with up to 30 carbon atoms, or a saturated or unsaturated straight-chain, branched or cyclic alkyl group with up to 30 carbon atoms and containing hetero atoms.

20. The process according to claim 16, wherein said (meth)acrylic acid ester is a methyl (meth)acrylate, an ethyl (meth)acrylate, a propyl (meth)acrylate, an isopropyl (meth) acrylate, a n-butyl (meth)acrylate, an isobornyl (meth) acrylate, a hydroxyalkyl (meth)acrylate, an aminoalkyl (meth)acrylate or mixtures thereof.

21. The process according to claim 20, wherein said hydroxyalkyl (meth)acrylate is selected from the group consisting of 2-hydroxyethyl (meth)acrylate, 2-hydroxypropyl (meth)acrylate, 3-hydroxypropyl (meth) acrylate, 3,4-dihydroxybutyl (meth)acrylate and mixtures thereof.

22. The process according to claim 16, wherein said salt of N-nitroso-N-phenylhydroxylamine is an ammonium salt, an aluminum salt, a copper salt, a lithium salt, a sodium salt, a potassium salt, or a rubidium salt.

23. The process according to claim 16, wherein said inhibitor is a dihydroxybenzene of Formula (II):

(II)

$$R^2O-\underset{R^1_n}{\bigcirc}-OH$$

wherein $R^1$ is a straight-chain or branched alkyl group with one to eight carbon atoms, halogen or aryl;
n is an integer ranging from one to four; and
$R^2$ is hydrogen, a straight-chain or branched alkyl group with one to eight carbon atoms or aryl.

24. The process according to claim 16, wherein said inhibitor is a 1,4 benzoquinone of Formula (III):

(III)

$$O=\underset{R^1_n}{\bigcirc}=O$$

where
$R^1$ is a straight-chain or branched alkyl group with one to eight carbon atoms, halogen or aryl; and
n is an integer ranging from one to four.

25. The process according to claim 16, wherein said inhibitor is a phenol of Formula (IV):

(IV)

$$HO-\bigcirc-R^1$$

wherein
$R^1$ is a straight-chain or branched alkyl group with one to eight carbon atoms, aryl, aralkyl, a propionic acid ester group with a monohydric to tetrahydric alcohol optionally containing hetero atoms.

26. The process according to claim 16, wherein said inhibitor is a triazine derivative of Formula (V):

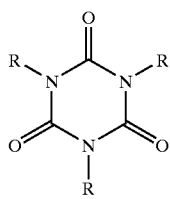

(V)

wherein

R=compound of Formula (VI)

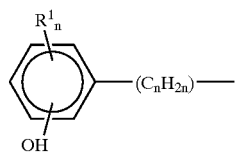

(VI)

wherein $R^1 = C_n H_{2n+1}$; and n=1 or 2.

27. The process according to claim 16, wherein said inhibitor is a pheneylenediamine of Formula (VII):

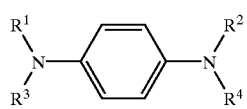

(VII).

wherein $R^1$, $R^2$, $R^3$ and $R^4$ independently are hydrogen or alkyl, aryl, alkaryl, aralkyl groups, each with up to 40 carbon atoms.

28. The process according to claim 27, wherein said phenylenediamine is selected from the group consisting of p-phenylenediamine, N-Phenyl-N'-alkyl-p-phenylene diamine, N-phenyl-N',N'-dialkyl-p-phenylenediamine, N,N-dialkyl-p-phenylenediamine, N,N'-dialkyl-p-phenylenediamine, N,N'-diaryl-phenylenediamine and N,N,N'-trialkyl-p-phenylenediamine.

29. The process according to claim 16, wherein said inhibitor is a phenazine dye selected from the group consisting of induline and nigrosine.

30. The process according to claim 16, wherein said inhibitor has a concentration of 0.01 to 0.5% by weight based on the total weight of said composition.

31. The process according to claim 17, wherein said solvent is selected from the group consisting of benzene, toluene, n-hexane, cyclohexane, methyl isobutyl ketone, methyl ethyl ketone and mixtures thereof.

32. The process according to claim 18, wherein said adjuvant is selected from the group consisting of an anti-binding agent, an antistatic, an antioxidant, a biostabilizer, a chemical propellant, a mold-release agent, a flame retardant, a lubricant, a dye, a casting improvement agent, a filler, a slip additive, an adhesion promoter, a catalyst, a photostabilizer, an optical brightener, an organic phosphorus compound, an oil, a pigment, an impact toughness improver, a reinforcing agent, a reinforcing fiber, an anti-weathering agent, a plasticizer and mixtures thereof.

33. A stabilized monomer composition, comprising:
(A) (i) at least one (meth)acrylic acid amide selected from the group consisting of N,N-dimethylaminopropyl methacrylamide, N,N-dimethylaminoethyl methacrylamide and a mixture thereof or (ii) at least one (meth)acrylic acid ester;
(B) N,N-diethylhydroxylamine;
(C) N-nitroso-N-phenylhydroxylamine or its salt; and
(D) a solvent selected from the group consisting of benzene, toluene, n-hexane, cyclohexane, methyl isobutyl ketone, methyl ethyl ketone and mixtures thereof;
wherein a weight ratio of N,N-diethylhydroxylamine to N-nitroso-N-phenylhydroxylamine or its salt is from 1:1 to 10:1;
wherein a concentration of N,N-diethylhydroxylamine is 10 to 500 ppm based on the total weight of said stabilized monomer composition; and
wherein a concentration of N-nitroso-N-phenylhydroxylamine or its salt is 10–500 ppm based on the total weight of said stabilized monomer composition.

34. The stabilized monomer composition according to claim 1, wherein said (meth)acrylic acid ester is represented by Formula (I):

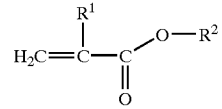

wherein
$R^1$ is hydrogen or a methyl group:
$R^2$ is an aryl group, an aryl group containing hetero atoms, a saturated or unsaturated straight-chain, branched or cyclic alkyl group with up to 30 carbon atoms, or a saturated or unsaturated straight-chain, branched or cyclic alkyl group with up to 30 carbon atoms and containing hetero atoms.

35. The stabilized monomer composition according to claim 1, wherein said (meth)acrylic acid ester is a methyl (meth)acrylate, an ethyl (meth)acrylate, a propyl (meth)acrylate, an isopropyl (meth)acrylate, a n-butyl (meth)acrylate, an isobornyl (meth)acrylate, a hydroxyalkyl (meth)acrylate, an aminoalkyl (meth)acrylate or mixtures thereof.

36. The stabilized monomer composition according to claim 35, wherein said hydroxyalkyl (meth)acrylate is selected from the group consisting of 2-hydroxyethyl (meth)acrylate, 2-hydroxypropyl (meth)acrylate, 3-hydroxypropyl (meth)acrylate, 3,4-dihydroxybutyl (meth)acrylate and mixtures thereof.

* * * * *